(12) United States Patent
Lu et al.

(10) Patent No.: US 6,392,068 B1
(45) Date of Patent: May 21, 2002

(54) CARBORANE CONTAINING CHOLESTEROL, A NEW TYPE OF MOLECULE FOR TARGETED BORON DRUG DELIVERY

(75) Inventors: Donghao Robert Lu; Bing Qing Ji, both of Athens, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/609,957

(22) Filed: Jul. 5, 2000

Related U.S. Application Data (60) Provisional application No. 60/143,053, filed on Jul. 7, 1999.

(51) Int. Cl.[7] ............................ C07J 9/00; A61K 31/69; A61K 31/56
(52) U.S. Cl. ................. 552/505; 552/505; 552/544; 514/64; 514/171; 514/182
(58) Field of Search ...................... 514/64, 171, 182; 552/505, 544

(56) References Cited

U.S. PATENT DOCUMENTS

| | | | |
|---|---|---|---|
| 4,516,535 A | 5/1985 | Russell, Jr. et al. | 128/1.1 |
| 4,959,356 A | 9/1990 | Miura et al. | 514/64 |
| 4,963,635 A | 10/1990 | Kinder et al. | 530/331 |
| 5,171,849 A | 12/1992 | Soloway et al. | 536/23 |

*Primary Examiner*—Sabiha Qazi
(74) *Attorney, Agent, or Firm*—Henry D. Coleman; R. Neil Sudol; William J. Sapone

(57) ABSTRACT

The present invention relates to novel carborane cholesterol analogs and their use in the treatment of tumor and cancers in humans, and in particular to the treatment of human brain tumors. Pharmaceutical compositions and methods of using these compositions in the treatment of tumors and cancer are other aspects of the present invention.

38 Claims, 4 Drawing Sheets

Cholesteryl 1,2-dicarba-closo-dodecaborane 1-carboxylate

Cholesteryl 1,12-dicarba-closo-dodecaborane 1-carboxylate

Cholesteryl 1,7-dicarba-closo-dodecaborane 1-carboxylate

FIGURE 1

Cholesteryl 1,2-dicarba-closo-dodecaborane 1-carboxylate

Cholesteryl 1,12-dicarba-closo-dodecaborane 1-carboxylate

Cholesteryl 1,7-dicarba-closo-dodecaborane 1-carboxylate

CARBORANE CONTAINING CHOLESTEROL, A NEW TYPE OF MOLECULE FOR TARGETED BORON DRUG DELIVERY

RELATED APPLICATIONS

This application derives the benefit of priority from provisional application serial No. 60/143,053, filed Jul. 7, 1999, entitled "Compounds and Methods for Use in Treating Tumors".

FIELD OF THE INVENTION

The present invention relates to novel carborane cholesterol analogs and their use in the treatment of tumor and cancers in humans, and in particular to the treatment of human brain tumors. Pharmaceutical compositions and methods of using these compositions in the treatment of tumors and cancer are other aspects of the present invention.

BACKGROUND OF THE INVENTION

Cancer continues to be a major cause of death in humans. Conventional treatment such as surgery, radiation therapy and chemotherapy have been extremely successful in certain cases. In other instances, alternative forms of cancer therapy involving the use of boron have been investigated. For example, Boron Neutron Capture Therapy ("BNCT") has been used to treat certain tumors for which conventional therapies have failed. Such therapies have helped treat Glioblastoma multiforme, a highly malignant, invasive form of brain cancer in Japan. BNCT is a two-step radiotherapy in which selective radioactive effect on tumor cells is achieved by targeting the tumor with non-radioactive $^{10}B$ and subsequently exposing it to neutrons. The nuclear reaction between $^{10}B$ and low energy neutrons creates high energy and particles, destroying those cells which contain $^{10}B$-containing agent.

BNCT is based on the nuclear reaction between thermal or epithermal neutrons, i.e., neutrons having energies of less than 0.5 eV to about 30–100 KeV, and Boron-10 to yield tumor-destroying alpha particles and Lithium-7 nuclei. In BNCT of malignant brain tumors, the patient is injected with a boron compound highly enriched in Boron-10. If designed correctly, the boronated compound concentrates preferentially in the brain tumor, not in the healthy surrounding tissues. A beam of thermal neutrons irradiate the patient's head and are then captured by the boron concentrated in the tumor. The tumor is thus irradiated with alpha particles whose range in tissue is about 10 $\mu$m or the diameter of an average cell. A localized, specific reaction takes place whereby the tumor receives a large radiation dose in comparison to that received by the surrounding healthy tissue. Shrinkage of tumor tissue results.

Various boron-containing compounds have been investigated for the clinical use of BNCT. Boronated analogs of compounds such as amino acids, thiouracils, chlorpromazine, nucleosides, antibodies, etc. have been the focus of compound development.

The boron-containing compound $Na_2B_{12}H_{11}SH$ (BSH) has been used in clinical trials. However, in-vitro experiments have shown that BSH does not stay in the tumor cell but is easily washed out. This may have accounted for the lack of success in some clinical trials.

Nucleosides have been proposed as alternative boron-containing compounds because such structures are proposed to be conserved by rapidly proliferating tumor cells and phosphorylated by cellular kinases to mononucleotides. These compounds can thus be localized to the tumor cell or can also be converted to the active precursors of nucleic acids, the di-and triphosphate forms.

BNCT-based nucleosides generally contain a single boron atom inserted into or linked or attached to the purine or pyrimidine base moiety. However, Soloway et al., in U.S. Pat. No. 5,171,849, have described a process for preparing carboranyl uridine nucleoside compounds and their diethyl ether adducts which exhibit a ten-fold increase in boron content over prior boron-containing compounds. Such introduction of a carboranyl moiety into or on the carbohydrate portion is also believed to enhance lipophilicity for cellular entrapment in proliferating tumor cells due to action of its structure and possible retention by cellular kinases or by the incorporation into an oligonucleotide which would hybridize strongly with RNA or DNA sequences. Additionally, the diether adducts of carboranyl uridine have enhanced hydrophilicity to enable solvation in aqueous media and can also be used in BNCT.

Michiko et al., in U.S. Pat. No. 4,959,356, have described the usage of porphrin compounds in BNCT. Porphrins are naturally occurring tetrapyrrole compounds normally found in plants and animals. They combine with metallic ions to produce a metalloporphrin important in metabolism. For example, Hemin is an iron-containing porphrin essential to blood. These porphrin compounds have preferential affinity for neoplastic tissue and can accumulate in tumors as shown by fluorescence which is produced by UV light activation of porphrins or metalloporphyrin.

The porphrin compounds can be employed as vehicles for the transport of boron to malignant tumors, especially brain tumors. The blood-brain barrier in mammals excludes the uptake of boronated porphyrin compounds into normal tissue and allows the accumulation of porphyrin compounds in tumor cells. Thus, upon irradiation, significant damage will be done to the tumor while leaving the healthy tissue intact. Typically, the patient's body is placed about 50 and 100 cm from the beam port.

Besides the type of boron carrier, methods for neutron-capture therapy have also been described. Russell et al., in U.S. Pat. No. 4,516,535, have noted that there has been a rapid attenuation of the thermal neutron flux which thus prevent effective treatment of deep-seated tumors. A large proportion of the neutrons never reach the tumor, but instead damage normal tissue. They have proposed the usage of an epithermal beam.

Thermal neutrons, which have energies of 0.5 eV or less, although more easily captured by the boron, are largely absorbed by the outer tissues before reaching the tumor. Epithermal (intermediate) neutrons with higher energies up to 100 KeV (preferred energy to 30 KeV), pass through outer layers of tissue and lose energy in the process. Then they are slowed to at or near the thermal energy range where they are subject to a high probability of capture by $B_{10}$. Fast neutrons, on the other hand, possess high energies and are highly destructive to tissue. Thus, a preferred epithermal beam should have low fluxes of destructive fast neutrons and thermal neutrons. Additionally, epithermal neutrons are effective in destroying subsurface tumors.

Russell and colleagues have used a filtered neutron beam that includes aluminum, sulfur and argon filters that provide a neutron "transmission" filter. This filter selectively transmits epithermal neutrons, absorbs thermal and fast neutrons, and attenuates harmful gamma radiation. These beams have a neutron flux greater than $10^7$ and preferably greater than about $5 \times 10^7$ neutrons/cm$_2$ sec. A preferred neutron energy distribution has less than about 15% and preferably less than 5% of the neutrons having energies above 30 KeV and a gamma radiation dosage within a medically acceptable range. Adjusting the ratio of thermal to epithermal neutrons changes the beam penetration to the proper depth for specific tumor location.

Generally, the patient is injected with a suitable dose of Na$_2$B$_{12}$H$_{11}$ SH (BSH) carried in a pharmaceutically acceptable medium between about 12 and about 24 hours prior to subjecting the patient to the filtered neutron beam. The patient is positioned between 50 and 100 cm from the beam port and in front of the beam of primarily epithermal neutrons.

In addition to the use of boron-containing compounds in BNCT, Kinder et al., in U.S. Pat. No. 4,963,655, have developed boronic acid analogues of amino acids that inhibit growth or colony formation in mammalian cells.

In cancer-related processes, increased protease enzyme activity ensues; such associated activity may be associated with the transformation of cells by viruses, chemicals, or other agents or with the metastatic potential of cancer cells. Data has suggested that protease inhibitors may prevent or reduce the incidence of transformation and reduce the metastatic potential. Kinder and collegues have described boronic acid analogues of amino acids which can act as protease inhibitors. In addition to the boronic acid analogues, they also showed a method of coupling boronic acid analogues of amino acids to other N-protected amino acid or N-protected dipeptides.

Antitumor agents generally work in the following manner. For example, they may be alkylating agents which bind covalently to DNA to form bifunctional lesions. Alternatively, they may function as antimetabolites which inhibit enzymes involved in DNA synthesis or assembly or serve as an analog substrate of DNA processes. Also, they may act as antibiotics which intercalate into the DNA helix or introducing strand breaks into DNA. Unlike these traditional mechanisms, the Kinder-described boron acid analogues function as protease inhibitors and mimic the transition state of serine-protease catalyzed peptide hydrolysis.

Normally, serine proteases hydrolyse peptide bonds by a nucleophillic attack of the serine OH in the active site of the enzyme on the carboxyl carbon of the substrate peptide bond. The nucleophilic attack forms a transient state. When boron is substituted for the carboxyl carbon at the reactive substrate site (e.g. where hydrolysis occurs). A stable-tight binding intermediate ensues.

Thus, these analogues inhibit the serine proteases elastase and chymotrypsin and also are cytotoxic against human and murine tumor cell in culture. However, the mechanism of cytotoxicity is still not fully understood. Further boron applications in cancer therapy are still yet to be defined.

OBJECTS OF THE INVENTION

It is an object of the present invention to provide novel carborane cholesterol compounds to be used in the treatment of tumors and cancer.

It is an additional object of the present invention to provide pharmaceutical compositions comprising novel carborane cholesterol compounds for use in the treatment of tumors and cancer, especially brain tumors.

It is another object of the present invention to provide methods for treating tumors and cancer which utilizes carborane cholesterol compounds according to the present invention.

It is a further object of the invention to provide a method for treating human brain tumors.

BRIEF DESCRIPTION OF THE INVENTION

The present invention is directed to novel carborane cholesterol compounds which find use as anti-neoplasia agents which make use of BNCT to treat cancer, in particular, malignant brain tumors. These compounds are based on carborane molecules to which are covalently bound cholesterol molecules. These compounds can be incorporated into low-density lipoprotein (LDL) and preferably are delivered directly to a brain tumor. The use of the carborane molecule allows efficient delivery of boron within a single molecule and the incorporation of a cholesterol moiety onto the carborane moiety allows utilization of a LDL receptor-mediated uptake mechanism which presents the possibility of long-term binding as well as internalization of the boron-containing molecule within the tumor cell. Efficient use of the present invention allows for unexpectedly effective radiation therapy to shrink and/or eliminate tumor tissue from the patient, especially brain tumor tissue.

The present invention also relates to a method for reducing the size of a tumor or eliminating the tumor or cancer from the patient by administering one or more compounds according to the present invention and after a period of time which allows the compound to localize within tumor cells or attach to tumor cells, the patient and compound are then exposed to an effective concentration of radiation energy in the form of neutrons preferably having a thermal and/or epithermal energy distribution (from less than about 5 eV to about 30 KeV or more) in order to shrink or eliminate the tumor.

DETAILED DESCRIPTION OF THE INVENTION

The term "patient" is used throughout the specification to describe an animal, generally a mammal and preferably a human, to whom treatment with the compositions according to the present invention is provided. For treatment of those conditions or disease states which are specific for a specific animal such as a human patient, the term patient refers to that specific animal.

The term "effective amount" is used throughout the specification to describe concentrations or amounts of compounds according to the present invention which may be used to produce a favorable change in the disease or condition treated, whether that change is a remission or a decrease in the growth or size of a tumor, depending upon the condition treated. The terms "effective amount" and "effective concentration" are used synonymously to describe the amount of radiation energy which is administered to a cancer patient in combination with one or more composition according to the present invention in order to effect therapy of a tumor, including a cancerous tumor or other cancer.

The term "neoplasia" is used to describe the pathological process that results in the formation and growth of a neoplasm, i.e., an abnormal tissue that grows by cellular proliferation more rapidly than normal tissue and continues to grow after the stimuli that initiated the new growth cease. Neoplasia exhibits partial or complete lack of structural organization and functional coordination with the normal tissue, and usually forms a distinct mass of tissue which may be benign (benign tumor) or malignant (carcinoma). The term "cancer" is used as a general term to describe any of various types of malignant neoplasms, most of which invade surrounding tissues, may metastasize to several sites and are likely to recur after attempted removal and to cause death of the patient unless adequately treated. As used herein, the term cancer is subsumed under the term neoplasia.

The term "carborane" is used to describe a cage-shaped molecule which has the formula $C_2B_{10}H_{12}$ and from which compounds according to the present invention are synthesized. As used in the present invention, carboranes exist in the para-, meta- and ortho-configurations (see below).

p-Carborane    o-Carborane    m-Carborane

Figure 1:
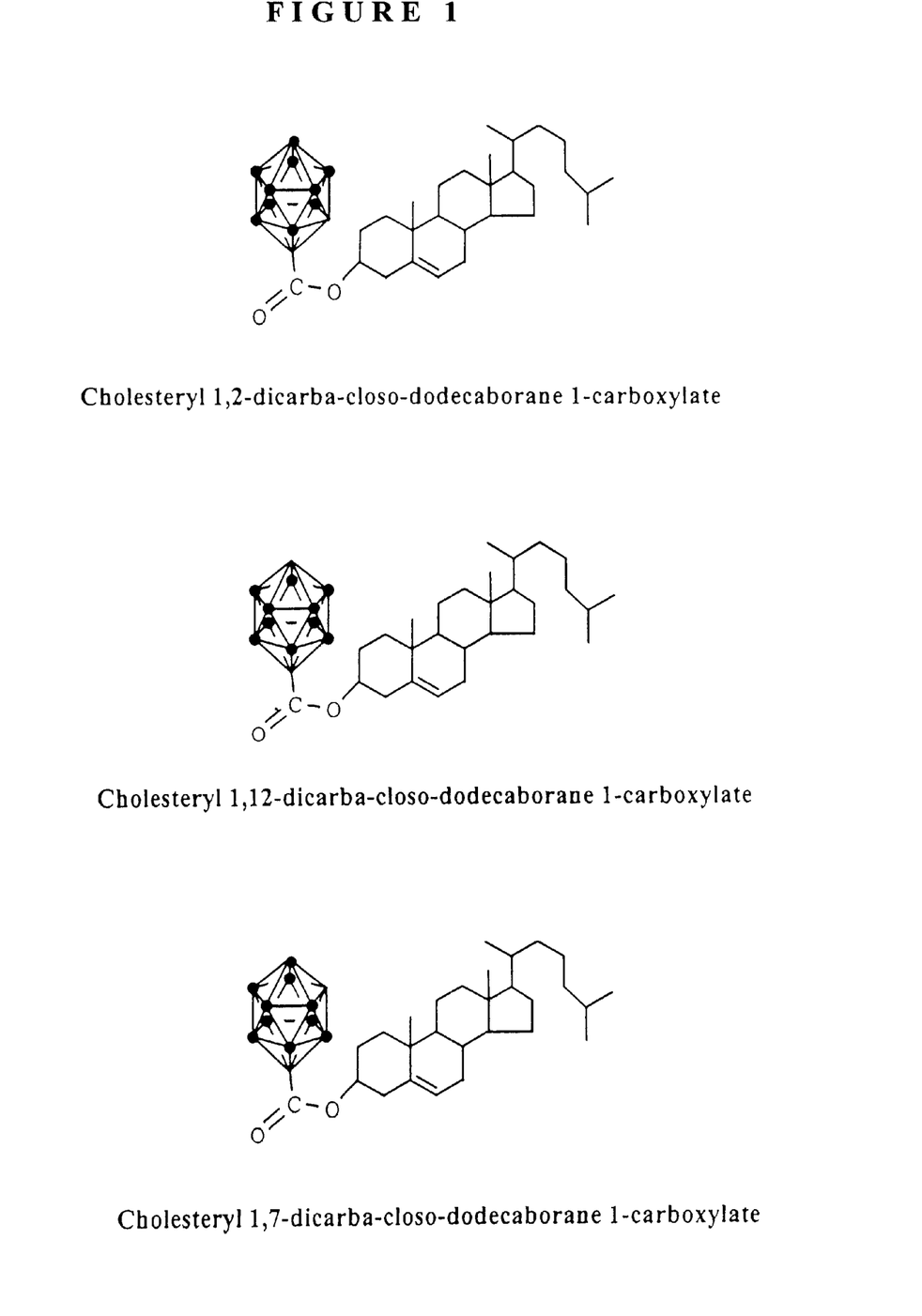
FIG. 1 is a pictorial representation of three cholesterol carborane compounds according to the present invention.

The term "cholesterol 1,12-dicarba-closo-dodecaborane 1-carboxylate" is used to describe a carborane cholesterol compound according to present invention which is derived from p-carborane and cholesterol. See FIG. 1.

The term "cholesterol 1,2-di-carba-closo-dodecaborane 1-carboxylate" is used to describe a carborane cholesterol compound according to present invention which is derived from o-carborsane and cholesterol. See FIG. 1.

The term "cholesterol 1,7-di-carba-closo-dodecaborane 1-carboxylate" is used to describe a carborane cholesterol compound according to present invention which is derived from m-carborane and cholesterol. See FIG. 1.

The term 'low-density lipoprotein" is used throughout the specification to describe complexes or compounds containing lipid and protein. Almost all of the lipids in plasma are presented and transported as lipoproteins. As used herein low-density lipoproteins are lipoproteins which are presented as being of low density (based upon their flotation constants between about 1.019–1.063). These generally appear in the, globulin fraction of plasma and are rich in triacylglyerols and cholesterol esters. The serum lipoproteins range in molecular weight from about 200,000 (preferably, at least about 2,000,000) to about 10,000,000 and a lipid content ranging from about 40–45% to about 80–85% by weight. As used herein, low-density lipoproteins are preferably combined with the carborane cholesterol compounds according to the present invention in a pharmaceutical dosage form.

The term "co-administration" is used throughout the specification to describe the administration of at least one compound according to the present invention in combination with another compound according to the present invention or an additional agent selected from the group consisting of anticancer agents, and in certain instances depending upon the desired therapy or target, antibiotics, antifungals, antinflammatories, or antiviral compounds. For example, in certain preferred embodiments of combination chemotherapy, compounds according to the present invention may be co-administered together or alternatively, with other anti-cancer or chemotherapeutic compounds, such compounds including, for example, the boron compounds borocaptate sodium (BSH) and borono-phenylalanine (BPA) or the chemotherapy agents cisplatin, etoposide, 1,3Bis[2-chloroethyl]-1-nitrosourea, cis-diammine-1,1-cyclobutane-dicarboxylate platinum (II) (carboplatin) or mixtures, thereof, among numerous others. In this aspect of the present invention the term co-administration embraces agents which are actually administered together (i.e., at the same time) or alternatively, compounds which are administered such that the blood or plasma concentations of the agents are sufficient to have a biological effect as therapeutic agents in the same patient at the same time, regardless of when the agents were actually administered.

A preferred therapeutic aspect according to the present invention relates to methods for treating neoplasia, including benign and malignant tumors and cancer in animal or human patients, and in preferred embodiments, brain tumors. This method comprises administering therapeutically effective amounts or concentrations of one or more of the compounds according to the present invention to inhibit the growth or spread of or to actually shrink the neoplasia in the animal or human patient being treated.

The carboranyl cholesterol compounds according to the present invention are used in boron neutron capture therapy (BNCT) of mammalian tumors. The tumors to be treated may be malignant or benign. The contemplated patients may include cows, pigs, horses, dogs, cats, sheep, goats, rodents and humans, etc. Representative target neoplasias which may be treated by the present invention include various cancers such as, stomach, colon, rectal, liver, pancreatic, lung, breast, ovary, prostate, testis, bladder, renal, brain/cns, head and neck, mouth/pharynx, oesophagus, larynx, melanoma, kidney and lymphoma, among others. Compounds according to the present invention are particularly useful in the treatment of brain tumors.

Pharmaceutical compositions based upon these novel chemical compounds comprise the above-described compounds in a therapeutically effective amount for the treatment of a condition or disease such as neoplasia, including brain tumors, or a related condition or disease optionally in combination with a pharmaceutically acceptable additive, carrier or excipient.

In the present invention, the use of the present compounds in water or saline, preferably in combination with a pharmaceutically acceptable carrier, as injectable dosage forms for intravenous injection is preferred. Administration of the present compounds is similar to other capture compounds for BNCT and suitable dosages, administration techniques, neutron radiation levels and times and techniques are similar to other capture compounds as known in the art. The compounds may be administered intravenously, directly into the tumor mass or through intracarotid or intracerebral administration. In certain preferred aspects according to the present invention, the carborane cholesterol compounds according to the present invention are combined with low-density lipoprotein in admixture and administered to the patient by injection the composition directly into the tumor.

In the present invention, the compounds are used in amounts which preferably lead to tumor cell uptake and eventual eradication of the tumor. Lesser amounts, which result in reducing the effects of the tumor (i.e., by shrinking the tumor, enhancing the appearance of the patient, hindering the growth of the tumor and/or prolonging the life of the patient) rather than eradicating the tumor, may also be used, but the goals of therapy as well as the amount and duration of therapy will vary according to the disease state and the age of the patient.

In certain pharmaceutical dosage forms, the pro-drug form of the compounds according to the present invention may be preferred. The present compounds or their derivatives, including prodrug forms of these agents, can be provided in the form of pharmaceutically acceptable salts or other complexes. As used herein, the term pharmaceutically acceptable salts or complexes refers to appropriate salts or complexes of the active compounds according to the present invention which retain the desired biological activity of the parent compound and exhibit limited toxicological effects to normal cells.

Modifications of the active compound can affect the solubility, bioavailability and rate of metabolism of the active species, thus providing control over the delivery of the active species. Further, the modifications can affect the anticancer activity of the compound, in some cases increasing the activity over the parent compound. This can easily be assessed by preparing the derivative and testing its anticancer activity according to known methods well within the routineer's skill in the art.

The compounds of this invention may be incorporated into formulations for all routes of parenteral administration including for example, intravenous, intracarotid, intracerebral, intramuscular and intraperitoneal suppository form.

Pharmaceutical compositions based upon these novel chemical compounds comprise the above-described compounds in a therapeutically effective amount for treating neoplasia, tumors and cancer, optionally in combination with a pharmaceutically acceptable additive, carrier and/or excipient. One of ordinary skill in the art will recognize that a therapeutically effective amount of one of more compounds according to the present invention will vary with the type and location of the neoplasia to be treated, its severity, the treatment regimen to be employed, the pharmacokinetics of the agent used, as well as the patient (animal or human) treated.

In the pharmaceutical aspect according to the present invention, the compound according to the present invention is formulated preferably in admixture with a pharmaceutically acceptable carrier, most preferably with at least one low-density lipoprotein. In general, it is preferable to administer the pharmaceutical composition parenterally, but a number of formulations may be administered via other routes of administration. Intravenous and intramuscular formulations are preferably administered in sterile saline, combined with an excipient, additive or carrier. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications which are well within the ordinary skill in the art. It is also well within the routineer's skill to modify the route of administration and dosage regimen of a particular compound in order to manage the pharmacokinetics of the present compounds for maximum beneficial effect to the patient.

The amount of compound included within therapeutically active formulations according to the present invention is an effective amount for treating cancer. In preferred aspects of the present invention, this amount is that which provides at least about approximately 10 ppm of boron in tumor cells, preferably at least about 30 ppm.

Compounds according to the present invention may be administered to a patient alone as the only active in the pharmaceutical composition, or alternatively, compounds according to the present invention may be co-administered together or alternatively, with other anti-cancer or chemotherapeutic compounds, such compounds including, for example, the boron compounds borocaptate sodium (BSH) and borono-phenylalanine)BPA) or the chemotherapy agents cisplatin, etoposide, 1,3Bis[2-chloroethyl]-1-nitrosourea, cis-diammine-1,1-cyclobutane-dicarboxylate platinum (II) (carboplatin) or mixtures, thereof., among numerous others.

Administration of the active compound may range from continuous (intravenous drip) to a single intravenous dose. Alternatively, a single injection of compositions according to the present invention directly into the tumor to be treated is also a preferred approach.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration.

For parenteral formulations, the carrier will usually comprise sterile water or aqueous sodium chloride solution, though other ingredients including those which aid dispersion may be included. In preferred aspects of the present invention, the compounds are intimately admixed with low-desnity lipoprotein of any type, provided that it is high in cholesterol. Of course, where sterile water is to be used and maintained as sterile, the compositions and carriers must also be sterilized. Injectable suspensions may also be prepared, in which case appropriate liquid carriers, suspending agents and the like may be employed.

The present compounds may be used to treat animals, and in particular, mammals, including humans, as patients. Thus, humans, equines, canines, bovines and other animals, and in particular, mammals, suffering from tumors, and in particular, cancer, or other related diseases as disclosed herein, can be treated by administering to the patient an effective amount of one or more of the compounds according to the present invention or its derivative or a pharmaceutically acceptable salt thereof optionally in a pharmaceutically acceptable carrier or diluent, either alone, or in combination with other known pharmaceutical agents, depending upon the disease to be treated. This treatment can also be administered in conjunction with other conventional cancer therapies, such as chemotherapy or surgery.

The active compound is included in the pharmaceutically acceptable carrier or diluent in an amount sufficient to deliver to a patient a therapeutically effective amount for the desired indication, without causing serious toxic effects in the patient treated.

The compound is conveniently administered in any suitable unit dosage form, including but not limited to one containing about 0.5 mg to 3000 mg, preferably 5 to 500 mg of active ingredient per unit dosage form. A dosage form for intracarotid or intracerebral administration of approximately 5 to 500 mg is usually convenient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

The active compound can also be mixed with other active materials that do not impair the desired action, or with materials that supplement the desired action, such as other anticancer agents, and in certain instances depending upon the desired therapy or target, antibiotics, antifungals, antiinflammatories, or antiviral compounds. For example, in certain preferred embodiments of combination chemotherapy, compounds according to the present invention may be co-administered together or alternatively, with other anti-cancer or chemotherapeutic compounds, such compounds including, for example, the boron compounds borocaptate sodium (BSH) and borono-phenylalanine)BPA) or the chemotherapy agents cisplatin, etoposide, 1,3Bis[2-chloroethyl]-1-nitrosourea, cis-diammine-1,1-cyclobutane-dicarboxylate platinum (II) (carboplatin) or mixtures, thereof, among numerous others.

Solutions or suspensions used for parenteral administration can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic. If administered intravenously, preferred carriers include, for example, physiological saline or phosphate buffered saline (PBS).

Liposomal suspensions may also be pharmaceutically acceptable carriers. These may be prepared according to methods known to those skilled in the art. For example, liposome formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Liposomal preparations which include cholesterol are preferred for use in this aspect of the present invention. Other methods of preparation well known by those of ordinary skill may also be used in this aspect of the present invention.

A wide variety of biological assays have been used and are accepted by those skilled in the art to assess anti-cancer activity of compounds. Any of these methods can be used to evaluate the activity of the compounds disclosed herein.

One common method of assessing activity is through the use of test panels of cancer cell lines. These tests evaluate the in vitro anti-cancer activity of particular compounds in cancer cell lines, and provide predictive data with respect to the use of tested compounds in vivo. Other assays include in vivo evaluations of the compound's effect on human or in an appropriate animal model, for example, using mouse tumor cells implanted into or grafted onto mice or in other appropriate animal models.

Chemical Synthesis

The carborane cholesterol compounds according to the present invention are synthesized via an acid chloride route or alternatively, in a coupling of the carboxylic acid to cholesterol using standard methods known in the art (Scheme I, below). In the acid chloride approach, carborane is first converted to its carboxylic acid using n-BuLi followed by $CO_2$. The respective carboxylic acid is then converted to the corresponding acyl halide using thionyl chloride or another chlorinating agent. The carborane acyl chloride is then reacted directly with cholesterol to form cholesteryl dicarba-closo-dodecaborane 1-carboxylate. Alternatively, the carborane carboxylic acid is coupled to cholesterol using dicyclohexylcarbodimide (DCC) and 4-(dimethylamino) pyridine (DMAP).

SCHEME 1

Neutron-capture therapy requires that the patient be injected with a compound that at least partially and preferably totally accumulates in a tumor. The accumulated portion of the molecule includes an element having an isotope which captures neutrons and emits a cell-destroying alpha particle. In the present invention, the amount of compound which accumulates in the tumor should be an amount which is sufficient so that the desired isotope, Boron, is present in the tumor in an amount of at least about 10 ppm, more preferably at least about 50 ppm, without being excessively toxic to the remaining cells and tissue of the patient.

In the present method, a patient to be subject to neutron capture therapy, is injected with at least one dose of the compound(s) according to the present invention, generally between about 1 and 48 hours, more preferably between about 12 and 24 hours, prior to radiation treatment. Alternatively, the compound may be administered for several days prior to radiation treatment. The approach is to accumulate boron within the tumor and preferably within the tumors cells in concentrations effective to provide tumor shrinkage when the compound is irradiated. For radiation treatment, the patient is generally positioned in front of the beam which primarily comprises primary epithermal neutrons. The tumor to be treated is generally placed in the direct path of the neutron beam. Typically, the patient's body or head is positioned about 50–100 centimers from the beam port, although the distance may vary with the type of radiation and instrumentation used.

For neutron therapy, in certain treatment regimens where the tumor or cancer is at or near the surface, neutrons having energies of less than about 0.5 eV (primarily within the thermal range) are preferred because they have the highest likelihood of capture. However, directing a beam of thermal neutrons at a patient having a tumor may be ineffective and may be harmful, especially in the case of tumors which are substantially below the surface of the skin. Therefore, in order to effectively treat brain tumors and other tumors which are substantially below the surface of the skin, epithermal neutrons having energies falling within the range of about 0.5 eV to 30 KeV will preferably be used. For purposes of destroying subsurface tumors, a beam highly enriched in intermediate or epithermal neutrons relative to thermal and fast neutrons (above 30 KeV) is preferred. In the case of beams comprising primarily or substantially large concentrations of fast neutrons (i.e., above 30 KeV), these tend to damage tissue and are less preferred for use in the present invention as it relates to treating subsurface tumors. In the case of treating surface tumors, the use of thermal or fast neutrons (greater than 30 KeV) may be more appropriate. Methods for delivering neutron beams of appropriate energy for use in BNCT for the treatment of tumors and cancer are described in U.S. Pat. No. 4,516,535, which is incorporated by reference herein.

In a preferred aspect of the present invention, in using the present compounds to treat tumors, the compounds are delivered to the tumor by intravenous delivery including intracarotid or intracerebral administration, for the treatment of brain tumors. Alternatively, the compounds may be injected directly into the tumor site, if it is accessible. The compounds may be preferably administered in liposomes or in conjunction with a low density lipoprotein (by incorporation into LDL prior to injection) or other means to target the compounds for delivery to cancer cells. The compounds allow sufficient boron atom delivery to the cells, which selectively incorporate the present compounds into cancer cells using an active transport system of the cell.

Having generally described the invention, reference is now made to the following examples intended to illustrate preferred embodiments and comparisons but which are not to be construed as limiting to the scope of this invention as more broadly set forth above and in the appended claims.

EXAMPLES

The following examples illustrate the invention. The synthesis of the carborane cholesterol compounds according to the present invention is presented in the following experiments. In general, where solvent is used, it is dried and distilled prior to use. Nitrogen is used dry at all times. All other materials are dried and distilled prior to use.

Experiment I

Figure 2:
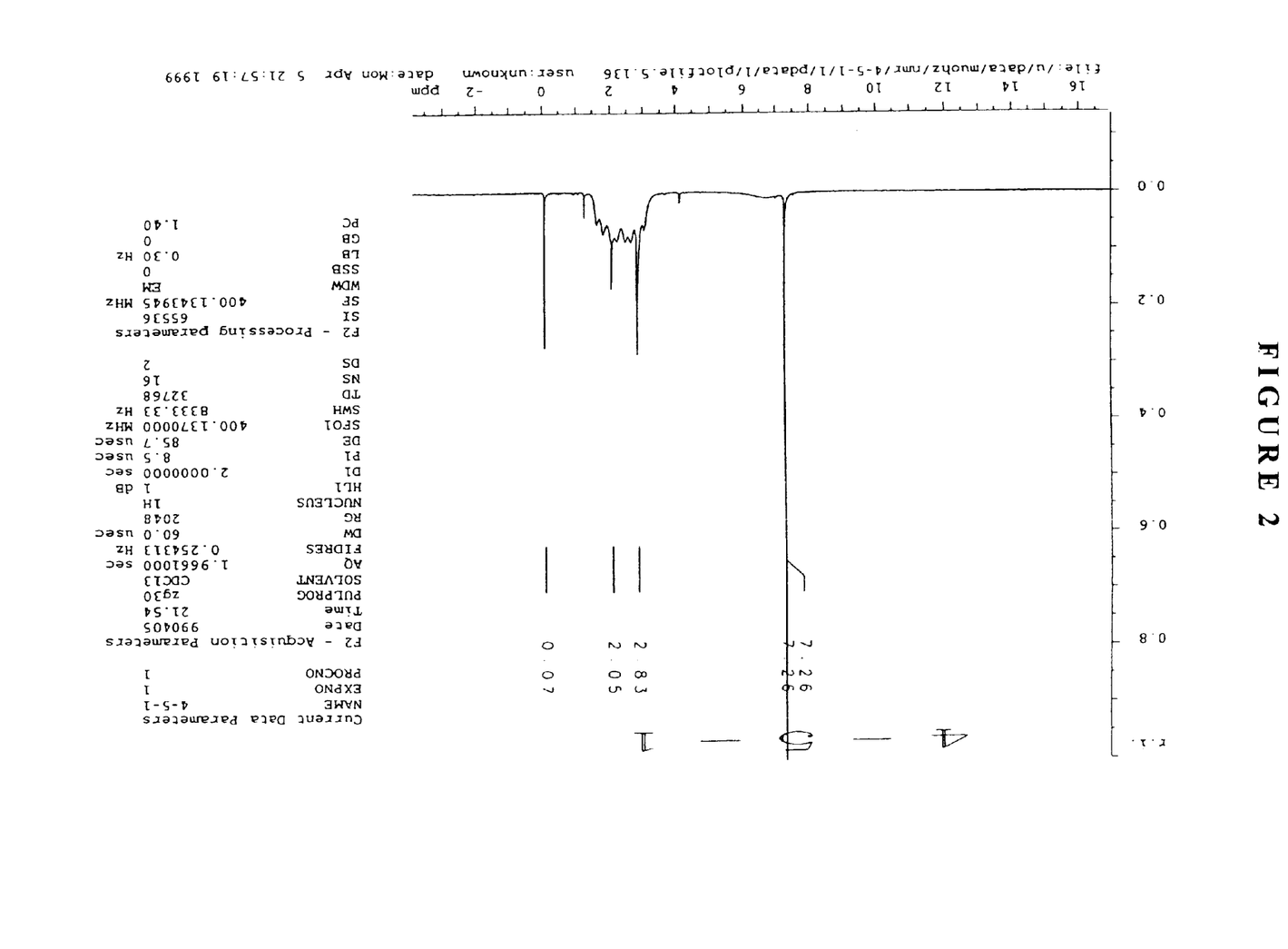
FIG. 2 is a proton NMR of 1-hydroxycarbonyl-1,12-dicarba-closo-dodecaborane, an intermediate in the synthesis of compounds according to the present invention.

Synthesis of Carborane acid (1-hydroxycarbonyl-1, 12-dicarba-closo-dodecaborane)

n-BuLi (1.1 ml, 1.66 mmol, 1.6 M in hexane) was slowly added to a stirred solution of p-carborane (200 mg, 1.38 mmol) in ether (80 ml) in a flask fitted with a reflux condenser at 0° C. The reaction mixture was warmed to room temperature and refluxed for 3 hr. The reflux condenser was removed and the reaction mixture was cooled to −78° C. (dry ice/ aceton). Dry ice ($CO_2$) was added to the reaction mixture under positive flow of nitrogen. The reaction mixture was allowed to warm to room temperature and excess ether was removed by vacuum. The residue was dissolved in 10 ml water and extracted with ether (2×5 ml). The aqueous layer was acidified with HCl solution (5M) to pH 1. The product extracted by ethyl acetate. Proton NMR and $^{13}C$ NMR have been used to confirm the structure of product. $^1H$ NMR ($CDCl_3$, 400 Hz) δ: 1.6–3.2(10H, B-H) (see FIG.2); $^{13}C$ NMR (400 Hz, DMSO-$d_6$) δ:166.58, 83.33;

Experiment II

Figure 3:
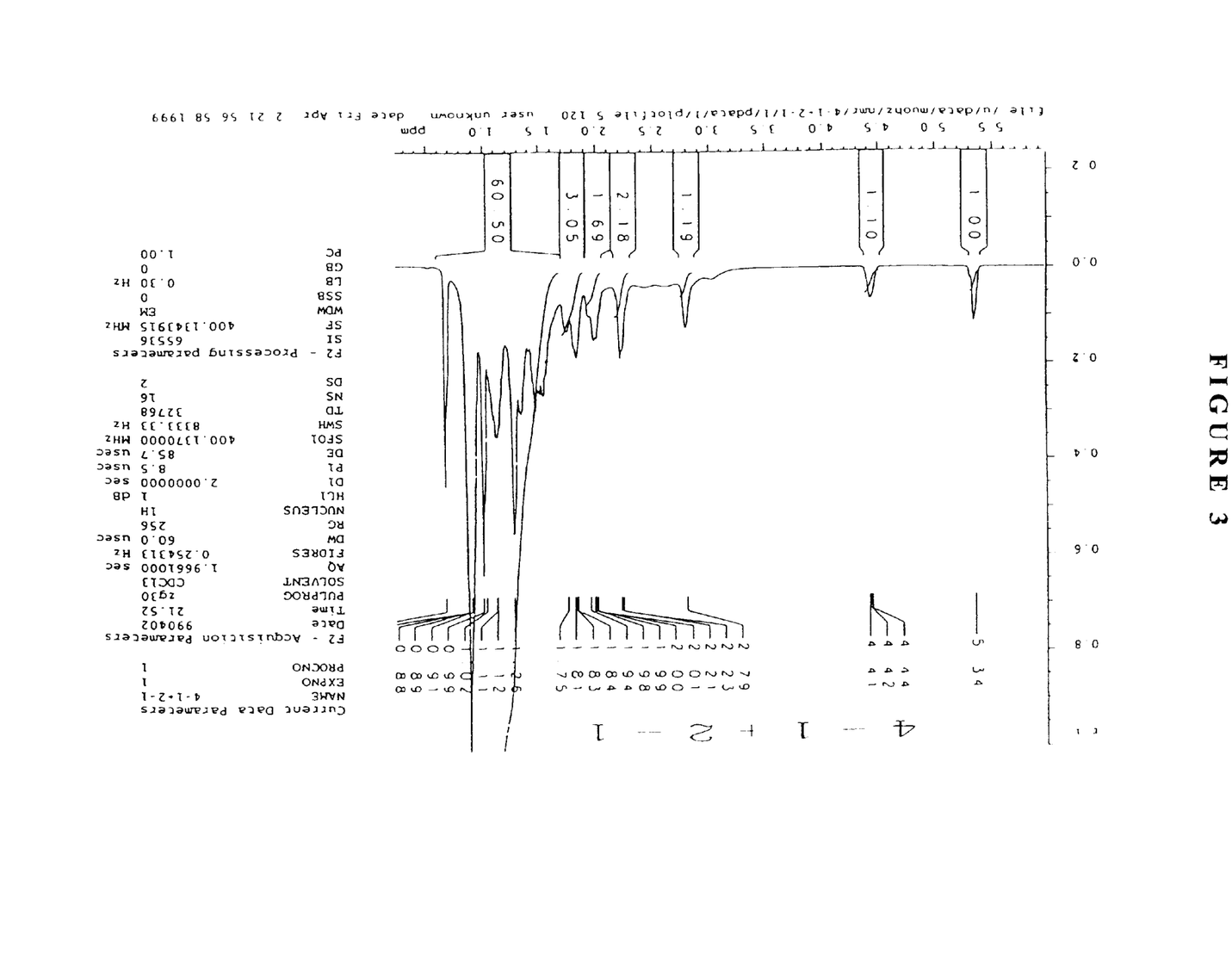
FIG. 3 is a proton NMR of cholesteryl 1,12-dicarba-closo-dodecaborane 1-carboxylate.
Figure 4:
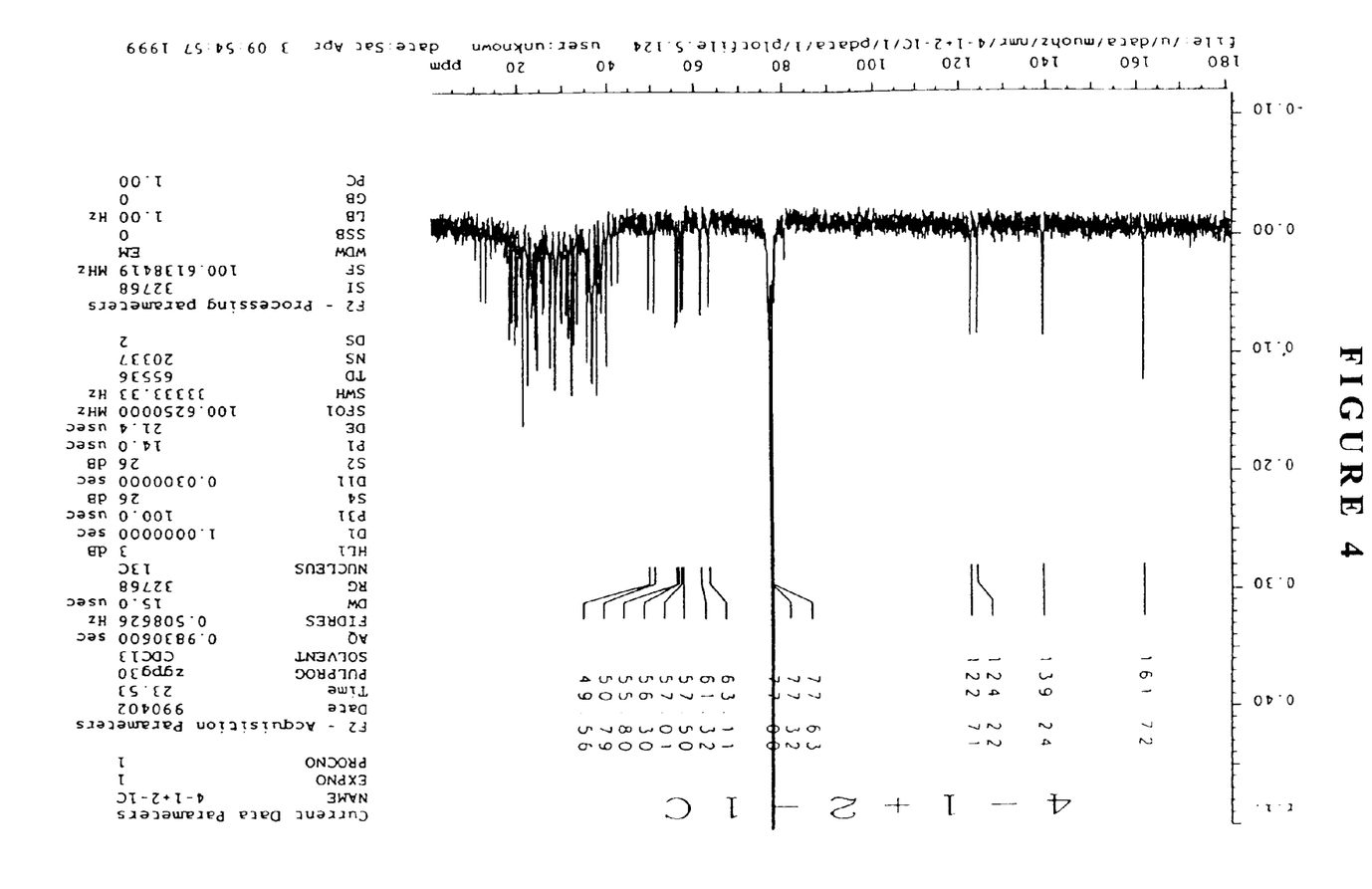
FIG. 4 is a $^{13}$C NMR of cholesteryl 1,12-dicarba-closo-dodecaborane 1-carboxylate.

Synthesis of cholesteryl 1,12-dicarba-closo-dodecaborane 1-carboxylate p-carborane carboxylic acid of 80 mg was placed in 25 ml flask. Thionyl chloride (5 ml) was added and the flask was quickly attached to reflux condenser protected by drying tube. The assembly was mounted in oil bath at 78° C. for 4 hr. Excess SO$_2$Cl was removed by vacuum. Cholesterol (160 mg) was dissolved in methylene chloride (3 ml) (containing pyridine 50 μl). The reaction mixture was stirred under nitrogen for 48 hr. The excess solvent was removed and residue was subject to column chromatography to separate the product from impurity. Proton NMR and $^{13}$C NMR have been used to confirm the structure of product. $^1$H NMR (CDCl$_3$, 400 Hz) δ: 1.6–5.1(10H, B-H), 5.34(1H, Chol 6), 4.43(1H,Chol 3)(see FIG.3); $^{13}$C NMR (CDCl$_3$) δ: 61.72 (acid 1), 139.24 (chol 5), 122.71 (Chol 6)(see FIG.4);

Experiment III

Synthesis of cholesteryl 1,12-dicarba-closo-dodecaborane 1-carboxylate

A mixture containing ρ-carborane carboxylic acid (80 mg, 0.4 mmol), cholesterol (180 mg, 0.4 mmol), DCC (dicyclohexylcarbodimide ) (80 mg, 0.4 mmol), DMAP (4-(dimethylamino) pyridine) (10 mg, 0.08 mmol) was stirred in 10 ml methylene chloride for 48 hr at room temperature. The reaction mixture was cooled to 0° C. and precipitate was filtrated. The filtrate was subject to silica gel column chromatography to purify the product: cholesteryl 1,12-dicarba-closo-dodecaborane 1-carboxylate. Proton NMR and $^{13}$C NMR have been used to confirm the structure of product. $^1$H NMR (CDCl$_3$, 400 Hz) δ: 1.6–5.1(10H, B-H), 5.34(1H, Chol 3)(see FIG. 3); $^{13}$C NMR (400 Hz, CDCl$_3$) δ: 61.72(acid 1), 139.24 (chol 5), 122.71(6)(see FIG. 4);

Each of the o-carborane cholesterol and m-carborane cholesterol compounds may be synthesized by analogy to the p-carborane cholesterol compound synthesized above substituting o-carborane or m-carborane for p-carborane in the syntheses. The remaining steps would proceed as they are presented, above.

It is to be understood that the examples and embodiments described hereinabove are for the purposes of providing a description of the present invention by way of example and are not to be viewed as limiting the present invention in any way. Various modifications or changes that may be made to that described hereinabove by those of ordinary skill in the art are also contemplated by the present invention and are to be included within the spirit and purview of this application and the following claims.

What is claimed is:

1. A compound for use in treating neoplasia selected from the group consisting of:
cholesterol 1,12-dicarba-closo-dodecaborane 1-carboxylate,
cholesterol 1,2-dicarba-closo-dodecaborane 1-carboxylate and
cholesterol 1,7-dicarba-closo-dodecaborane 1-carboxylate.

2. The compound according to claim 1 which is cholesterol 1,12-dicarba-closo-dodecaborane 1-carboxylate.

3. The compound according to claim 1 which is cholesterol 1,2-dicarba-closo-dodecaborane 1-carboxylate.

4. The compound according to claim 1 which is cholesterol 1,7-dicarba-closo-dodecaborane 1-carboxylate.

5. A pharmaceutical composition for use in treating neoplasia comprising an effective amount of a compound selected from the group consisting of:
cholesterol 1,12-dicarba-closo-dodecaborane 1-carboxylate,
cholesterol 1,2dicarba-closo-dodecaborane 1carboxylate,
cholesterol 1,7-dicarba-closo-dodecaborane 1-carboxylate and mixture thereof.

6. The composition according to claim 5 wherein said compound is formulated in combination with a pharmaceutically acceptable additive, excipient or carrier.

7. The composition according to claim 6 wherein said compound is cholesterol 1,12-dicarba-closo-dodecaborane 1-carboxylate.

8. The composition according to claim 7 wherein said compound is cholesterol 1,2-dicarba-closo-dodecaborane 1-carboxylate.

9. The composition according to claim 8 wherein said compound is cholesterol 1,7-dicarba-closo-dodecaborane 1-carboxylate.

10. The composition according to claim 5 wherein said compound is formulated in combination with liposomes.

11. The composition according to claim 10 wherein said compound is cholesterol 1,12-dicarba-closo-dodecaborane 1-carboxylate.

12. The composition according to claim 10 wherein said compound is cholesterol 1,2-dicarba-closo-dodecaborane 1-carboxylate.

13. The composition according to claim 10 wherein said compound is cholesterol 1,7-dicarba-closo-dodecaborane 1-carboxylate.

14. The composition according to claim 5 wherein said compound is incorporated into liposomes as a pharmaceutical dosage form.

15. The composition according to claim 5 wherein said compound is formulated in combination with at least one additional agent selected from the group consisting of borocaptate sodium, borono-phenylalanine, cisplatin, etoposide, 1,3Bis[2-chloroethyl]-1-nitrosourea, cis-diammine-1,1-cyclobutane-dicarboxylate platinum (II), or mixtures, thereof.

16. The composition according to claim 6 wherein said compound is formulated in combination with at least one additional agent selected from the group consisting of borocaptate sodium, borono-phenylalanine, cisplatin, etoposide, 1,3Bis[2-chloroethyl]-1-nitrosourea, cis-diammine-1,1-cyclobutane-dicarboxylate platinum (II), or mixtures, thereof.

17. A method of treating a patient with a malignant tumor comprising:
administering to the patient a dose of a boron neutron capture compound selected from the group consisting of
cholesterol 1,12-dicarba-closo-dodecaborane 1-carboxylate,
cholesterol 1,2-dicarba-closo-dodecaborane 1-carboxylate,
cholesterol 1,7-dicarba-closo-dodecaborane 1-carboxylate and mixtures thereof, in an amount effective to accumulate in said tumor and emit alpha particles to substantially shrink said tumor when said compound and said tumor are exposed to neutron radiation; and exposing said tumor and said compound to a neutron radiation beam for a duration and at a concentration to emit alpha particles from said compound to shrink said tumor.

18. The method according to claim 17 wherein said neutron energy ranges from about 0.5 eV to about 30 KeV.

19. The method according to claim 17 wherein said neutron radiation beam has an energy distribution such that no more than about 30 percent of the neutrons in said beam have energies which are less than about 0.5 eV and no more than 15 percent of the neutrons in said beam have energies which are greater than about 30 KeV and has an incident gamma radiation dose rate within medically acceptable limits.

20. The method according to claim 17 wherein said compound is co-administered with at least one additional agent selected from the group consisting of borocaptate sodium, borono-phenylalanine, cisplatin, etoposide, 1,3Bis[2-chloroethyl]-1-nitrosourea, cis-diammine-1,1-cyclobutane-dicarboxylate platinum (II), or mixtures, thereof.

21. The method according to claim 17 wherein said tumor is cancerous.

22. The method according to claim 21 wherein said compound is co-administered with at least one additional agent selected from the group consisting of borocaptate sodium, borono-phenylalanine, cisplatin, etoposide, 1,3Bis[2-chloroethyl]-1-nitrosourea, cis-diammine-1,1-cyclobutane-dicarboxylate platinum (II), or mixtures, thereof.

23. The method according to claim 17 wherein said tumor is a brain tumor.

24. The method according to claim 18 wherein said tumor is a brain tumor.

25. The method according to claim 19 wherein said tumor is a brain tumor.

26. A method of treating a patient with a tumor comprising:
administering to the patient a dose of a compound selected from the group consisting of
cholesterol 1,12-dicarba-closo-dodecaborane 1-carboxylate,
cholesterol 1,2-dicarba-closo-dodecaborane 1-carboxylate,
cholesterol 1,7-dicarba-closo-dodecaborane 1-carboxylate and mixtures thereof, in an amount effective to accumulate in said tumor and emit alpha particles to substantially shrink said tumor when said compound and said tumor are exposed to neutron radiation; and exposing said tumor and said compound to an effective amount of neutron radiation for a duration and at a concentration to emit alpha particles from said compound to shrink said tumor.

27. The method according to claim 26 wherein said neutron energy ranges from about 0.5 eV to about 30 KeV.

28. The method according to claim 26 wherein said neutron radiation beam has an energy distribution such that no more than about 30 percent of the neutrons in said beam have energies which are less than about 0.5 eV and no more than 15 percent of the neutrons in said beam have energies which are greater than about 30 KeV and has an incident gamma radiation dose rate within medically acceptable limits.

29. The method according to claim 26 wherein said tumor is a brain tumor.

30. The method according to claim 26 wherein said compound is administered to said patient by intracarotid, intracerebral or intravenous administration.

31. The method according to claim 26 wherein said compound is administered to said patient in combination with liposomes.

32. The method according to claim 31 wherein said compound is administered to said patient by intracarotid, intracerebral or intravenous administration.

33. The method according to claim 26 wherein said tumor is a brain tumor.

34. The method according to claim 31 wherein said tumor is a brain tumor.

35. The method according to claim 32 wherein said tumor is a brain tumor.

36. The method according to claim 26 wherein said compound is co-administered with an agent selected from the group consisting of borocaptate sodium, borono-phenylalanine, cisplatin, etoposide, 1,3Bis[2-chloroethyl]-1-nitrosourea, cis-diammine-1,1-cyclobutane-dicarboxylate platinum (II), or mixtures, thereof.

37. The method according to claim 26 wherein said compound is co-administered with an agent selected from the group consisting of borocaptate sodium, borono-phenylalanine, cisplatin, etoposide, 1,3Bis[2-chloroethyl]-1-nitrosourea, cis-diammine-1,1-cyclobutane-dicarboxylate platinum (II), or mixtures, thereof.

38. The method according to claim 26 wherein said tumor is a malignant glioma of the brain.

\* \* \* \* \*